US 8,105,470 B2

(12) United States Patent
Matsui et al.

(10) Patent No.: US 8,105,470 B2
(45) Date of Patent: Jan. 31, 2012

(54) SENSOR

(75) Inventors: Noboru Matsui, Aichi (JP); Tomohiro Nakamura, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 394 days.

(21) Appl. No.: 12/397,926

(22) Filed: Mar. 4, 2009

(65) Prior Publication Data
US 2009/0223818 A1  Sep. 10, 2009

(30) Foreign Application Priority Data

Mar. 6, 2008 (JP) ................................. 2008-056946

(51) Int. Cl.
*G01N 27/407* (2006.01)
(52) U.S. Cl. ......... 204/426; 204/424; 204/425; 204/428
(58) Field of Classification Search ................. 204/424, 204/425, 426, 428
See application file for complete search history.

(56) References Cited

U.S. PATENT DOCUMENTS

| | | | |
|---|---|---|---|
| 4,556,475 A | 12/1985 | Bayha et al. | |
| 2003/0074950 A1 | 4/2003 | Yamada et al. | |
| 2005/0145013 A1* | 7/2005 | Hayashi et al. | 73/31.05 |
| 2006/0220159 A1* | 10/2006 | Matsuo et al. | 257/414 |
| 2006/0237315 A1* | 10/2006 | Matsuo et al. | 204/424 |
| 2006/0288759 A1* | 12/2006 | Okumura et al. | 73/31.05 |
| 2007/0119235 A1* | 5/2007 | Matsuo et al. | 73/31.05 |
| 2007/0243760 A1* | 10/2007 | Fujita et al. | 439/585 |
| 2010/0139364 A1* | 6/2010 | Kume et al. | 73/23.31 |
| 2010/0139379 A1* | 6/2010 | Kume et al. | 73/114.73 |

FOREIGN PATENT DOCUMENTS

| | | |
|---|---|---|
| EP | 1677104 A | 7/2006 |
| JP | 2004251729 A | 9/2004 |
| JP | 2007-047093 A | 2/2007 |

* cited by examiner

*Primary Examiner* — Bruce Bell
(74) *Attorney, Agent, or Firm* — Sughrue Mion, PLLC

(57) ABSTRACT

A sensor (1) including a plate-shaped sensor element (21) extending in a front-rear direction and having at least 3 electrode terminals (25) provided on at least one side surface (24) of the sensor element at intervals in a lateral direction; a plurality of metallic terminal members (51a, 51b) connected to the electrode terminals (25) of the sensor element (21); and a separator (71) surrounding and insulating the plurality of metallic terminal members (51a, 51b). The metallic terminal members (51a, 51b) each has a crimp portion (57a, 57b) formed at a rear end thereof and a lead wire (61) is crimp-connected to the crimp portion (57a, 57b). The crimp portions (57a) located at opposite sides with respect to the lateral direction face the side surface (24) of the sensor element (21), whereas the crimp portion (57b) faces away from the side surface (24) of the sensor element (21).

5 Claims, 14 Drawing Sheets

SENSOR

BACKGROUND OF THE INVENTION

1. Field of the Invention

The present invention relates to a sensor, and more particularly, to a sensor such as a gas sensor (e.g., an oxygen sensor, an NOx sensor, or an HC sensor) for detecting the concentration of a specific gas component in exhaust gas exhausted from, for example, an internal combustion engine, or a temperature sensor for detecting the temperature of the exhaust gas.

2. Description of the Related Art

Conventionally, a gas sensor has been used for air-fuel-ratio control of an automobile. Such a gas sensor includes a sensor element whose electrical characteristics change in accordance with the concentration of a specific gas component within exhaust gas (Patent Document 1). FIG. 12 shows such a gas sensor (hereinafter also referred to as a "sensor") 1. This gas sensor 1 includes a sensor element (hereinafter also referred to as an "element") 21 formed of a solid electrolyte having oxygen-ion conductivity; a metallic shell body 11 for holding the sensor element 21; a metallic protection sleeve 81 provided at a rear end (an upper end in FIG. 12) of the metallic shell body 11; metallic terminal members 51 electrically connected to electrode terminals 25 provided on side surfaces 24 of a rear end portion of the sensor element 21; lead wires 61 connected to the metallic terminal members 51 and extended outward from the rear end of the protection sleeve 81; a separator 71 disposed within the protection sleeve 81 so as to insulate the plurality of metallic terminal members 51 and the lead wires 61 connected thereto; an elastic seal member 101 through which the lead wires 61 are extended to the outside of the protection sleeve 81 and which seals the protection sleeve 81; etc. Notably, in the present specification, when the term "rear end" is used for the sensor 1, its component, or a section (portion) thereof, it refers to an upper end of the sensor, component, or the like in FIG. 12. Also, when the term "front end" is used for the sensor 1, its component, or a section (portion) thereof, it refers to a lower end of the sensor, component, or the like in FIG. 12.

In the sensor 1 having the above-described structure, the separator 71 is formed of an electrically insulative material such as ceramic, and includes terminal spaces 75 formed therein such that the spaces 75 penetrate the separator 71 in the front-rear direction, as shown in FIGS. 12 and 13. The metallic terminal members 51 are positioned and accommodated within the respective spaces 75, so as to insulate the metallic terminal members 51 and the lead wires 61. The respective metallic terminal members 51 are formed from a metal plate by pressing and bending operations. A plate spring portion 53 is provided at the front end of each of the metallic terminal members 51, and is resiliently pressed against the corresponding electrode terminal 25 provided on the side surface 24 of the sensor element 21 by means of the plate spring portion 53. In this manner, the metallic terminal member 51 is electrically connected to the electrode terminal 25. Further, the metallic terminal members 51 each has a crimp portion 57 formed at the rear end thereof such that the crimp portion 57 connects to the plate spring portion 53 via a junction line portion 55. By crimping the crimp portion 57, the metallic terminal member 51 is connected to the conductor of a corresponding lead wire 61. The lead wires 61 are passed through lead-wire passage through holes 105 formed in the elastic seal member 101 such that the holes penetrate in the front-rear direction, and are extended to the outside.

In the conventional sensor 1 having the above-described structure, the sensor element 21 assumes the form of an elongated plate. As shown in FIG. 12, for example, three electrode terminals 25 are laterally arranged on one side surface 24 of the rear end portion of the sensor element 21. Similarly, for example, two electrode terminals 25 are laterally arranged on the other side surface 24 of the sensor element 21 at the rear end thereof. Meanwhile, the metallic terminal members 51 are disposed so as to be laterally arranged in the terminal spaces 75 of the separator 71, and, as described above, the plate spring portions 53 are electrically connected to corresponding electrode terminals 25 within the terminal spaces 75. In this sensor 1, the conductors of the lead wires 61 are connected to the crimp portions 57 of the corresponding metallic terminal members 51 by bending crimping fingers 58 of the crimp portions 57 toward the side where the electrode terminals 25 of the sensor element 21 are present (on the side where an axis G is present in FIG. 12).

[Patent Document 1] Japanese Patent Application Laid-Open (kokai) No. 2007-47093

3. Problems to be Solved by the Invention

Incidentally, in the sensor 1 having the above-described structure, the elastic seal member 101 is compressed in the radial direction when a smaller-diameter portion 83 at the rear end of the protection sleeve 81 is circumferentially crimped in a state in which the lead wires 61 are passed through the through holes 105. As a result, sealing is established at, among other locations, the through holes 105 through which the lead wires 61 are passed. In such a structure, from the viewpoint of sealing performance, the lead wires 61 passing through the through holes 105 are preferably compressed as uniformly and efficiently as possible. For such uniform and efficient compression, the through holes 105 are desirably disposed as follows. Since in general the elastic seal member 101 has a roughly circular transverse cross section (a shape as viewed in the front-rear direction of the sensor 1) as shown in FIG. 14, the through holes 105 are desirably disposed along a circle (imaginary circle) concentric with the transverse cross section at equal angular intervals or intervals similar thereto such that the through holes 105 are located as close as possible to the outer circumferential edge of the transverse cross section. Therefore, in the sensor 1 of FIG. 12, a through hole (hereinafter also referred to as the "center through hole") 105, which is one of the through holes 105 corresponding to one side surface 24 carrying the laterally arranged three electrode terminals 25 and through which the lead wire 61 connected to the center metallic terminal member is passed, is desirably provided such that the center through hole 105 is located outward in relation to through holes (hereinafter also referred to as the "side through holes") 105 through which the lead wires 61 connected to the side metallic terminal members located at opposite lateral ends are passed, as viewed from the rear side.

However, the metallic terminal members 51 connected to the electrode terminals 25 of the sensor element 21 in the above-described manner are disposed within the terminal spaces 75 of the separator 71 such that the metallic terminal members 51 are laterally arranged to face the electrode terminals 25 (see FIG. 13). Therefore, under the assumption that the entirety of each metallic terminal member 51, excluding the plate spring portion 53, is approximately straight, the crimp portions 57 of the metallic terminal members 51 are also laterally arranged. Accordingly, for example, measures as described below must be taken in order to enable the lead wire 61 connected to the center metallic terminal member 51 to be passed through the center through hole 105 of the elastic seal member 101 and extended to the outside.

According to one measure, the crimp portion 57 of the center metallic terminal member 51 is separated from the corresponding electrode terminal 25 of the sensor element 21 as viewed from the rear side. That is, the junction line portion 55 between the plate spring portion 53 and the crimp portion 57 is bent into, for example, a crank shape, so as to separate the crimp portion 57 from the corresponding electrode terminal 25. According to another measure, a clearance is formed along the front-rear direction between the separator 71 and the elastic seal member 101 without deforming the metallic terminal members 51, and a front end of the lead wire 61 connected to the crimp portion 57 of the center terminal electrode 51 is bent into a crank shape.

However, the measure of bending the metallic terminal member 51 or the front end of the lead wire 61 within the small sensor 1 is not so easily accomplished, and an increase in the size of the sensor is unavoidable. That is, in order to allow for such bending, the size of the separator 71 must be increased, or a large space within the sensor which extends in the direction of the axis G (the front-rear direction) must be secured. For example, in the case where a metallic terminal member 51 whose junction line portion 55 is bent is accommodated within the corresponding terminal space 75 of the separator 71, the length and cross-sectional area of the space 75 must be increased. Further, in the case where the lead wire 61 is bent, a clearance must be formed along the front-rear direction between the separator 71 and the elastic seal member 101 with a resultant increase in the size of the sensor.

SUMMARY OF THE INVENTION

The present invention has been accomplished in view of the above problems, and an object thereof is to provide a sensor which is configured such that a center through hole of an elastic seal member is located outward in relation to the remaining through holes thereof, as in the case of the above-described elastic seal member, and a lead wire connected to a center metallic terminal member is passed through the center through hole and extended to the outside, and in which the lead wire can be passed through the center through hole and extended to the outside without bending the metallic terminal member or the lead wire, or with the metallic terminal member or the lead wire being bent by a reduced amount.

The above has been achieved in a first aspect of the invention by providing a sensor comprising a plate-shaped sensor element extending in a front-rear direction and having a plurality of electrode terminals; a plurality of metallic terminal members connected to the electrode terminals of the sensor element; and a separator surrounding and insulating the plurality of metallic terminal members, wherein at least three electrode terminals are provided on at least one side surface of the sensor element at intervals in a lateral direction normal to the front-rear direction;

individual ones of the plurality of metallic terminal members each has a plate spring portion formed at a front end thereof, and a crimp portion formed at a rear end thereof and connecting to the plate spring portion;

the plate spring portion is pressed against the corresponding electrode terminal to thereby electrically connect the plate spring portion to the electrode terminal;

a lead wire is crimp-connected to the crimp portion to thereby electrically connect the lead wire to the crimp portion; and the lead wire is passed through one of a plurality of through holes of an elastic seal member disposed on the rear-end side of the separator, and is extended to the outside, the through holes being formed in the elastic seal member generally along a circle.

In the sensor having such a structure, of the metallic terminal members connected to the at least three electrode terminals, side metallic terminal members located at opposite ends with respect to the lateral direction are crimp-connected to lead wires by means of crimping fingers of the crimp portions of the side metallic terminal members that are bent toward the side where the electrode terminals are present; and a remaining metallic terminal member is crimp-connected to a lead wire by means of crimping fingers of the crimp portion of the remaining metallic terminal member that are bent toward the side opposite the side where the electrode terminals are present.

In a second aspect, the present invention provides a sensor comprising a plate-shaped sensor element extending in a front-rear direction and having a plurality of electrode terminals; a plurality of metallic terminal members connected to the electrode terminals of the sensor element; and a separator surrounding and insulating the plurality of metallic terminal members, wherein at least three electrode terminals are provided on at least one side surface of the sensor element at intervals in a lateral direction normal to the front-rear direction;

individual ones of the plurality of metallic terminal members each has a plate spring portion formed at a front end thereof, and a crimp portion formed at a rear end thereof and connecting to the plate spring portion;

the plate spring portion is pressed against the corresponding electrode terminal to electrically connect the plate spring portion to the electrode terminal;

a lead wire is crimp-connected to the crimp portion to electrically connect the lead wire to the crimp portion; and the lead wire is passed through one of a plurality of through holes of an elastic seal member disposed on the rear-end side of the separator, and is extended to the outside, the through holes being formed in the elastic seal member generally along a circle.

In the sensor having such a structure, the separator comprises a first separator located on the front end side and a second separator located on the rear end side;

of the metallic terminal members connected to the at least three electrode terminals, side metallic terminal members located at opposite ends with respect to the lateral direction are crimp-connected to lead wires by means of crimping fingers of the crimp portions of the side metallic terminal members that are bent toward the side where the electrode terminals are present;

a remaining metallic terminal member is crimp-connected to a lead wire by means of crimping fingers of the crimp portion of the remaining metallic terminal member that are bent toward the side opposite the side where the electrode terminals are present;

the plate spring portions of the metallic terminal members are accommodated in terminal spaces formed in the first separator; and the crimp portions of the metallic terminal members are accommodated in terminal spaces formed in the second separator, wherein rearward movement of the crimp portions of the metallic terminal members is blocked at rear ends of the terminal spaces of the second separator.

In a preferred embodiment according to either of the first or second aspects of the invention, individual ones of the plurality of metallic terminal members each has a junction line portion which connects the crimp portion and the plate spring portion and which extends straight in the front-rear direction of the sensor element.

EFFECTS OF THE INVENTION

According to the first aspect of the invention, the following effects are achieved. The effects will be described by reference to an example case where three electrode terminals are provided on one side surface of the element at intervals in the lateral direction. In the case where three electrode terminals are arranged laterally, as viewed from the rear side, the crimp portion (hereinafter also referred to as the "center crimp portion") of a metallic terminal member connected to the electrode terminal located at the center is separated outward and faces away from the one side surface of the sensor element by a greater distance, as compared with the crimp portions (hereinafter also referred to as the "side crimp portions") of the remaining metallic terminal members which face toward the one side surface of the sensor element. Accordingly, even in the case where the through holes of the elastic seal member are arranged generally along a circle, the lead wires can be passed through the through holes more easily, as compared with the case where all the crimp portions face toward the side where the electrode terminals of the sensor elements are present. That is, according to the first aspect of the invention, even when the through holes of the elastic seal member are arranged along a circle or at positions near the circle, the center metallic terminal member or the lead wire connected thereto need not be bent or bending is only required to a reduced degree. This is because the crimp portion of the center metallic terminal member is positioned outward and faces away from the one side surface of the sensor element in relation to the other crimp portions of the side metallic terminal members which face toward the one side surface of the sensor element. Therefore, the lead wire can be smoothly passed through the center through hole and extended to the outside.

According to the second aspect of the invention, the following effects are achieved. The separator must be designed such that its size does not increase. Further, the separator must provide electrical insulation among the metallic terminal members and between the metallic terminal members and an outside protection tube. In addition, when an external pulling force is applied to the lead wires, the sensor must provide sufficient resistance to the force. Therefore, in general, an engagement finger which engages the front end of the separator is provided at, for example, the distal end of the plate spring portion of each metallic terminal member. However, in some cases, difficulty may arise in providing the engagement finger, from the viewpoint of assembly. The sensor according to the second aspect of the invention can easily cope with such requirements as explained in detail below.

In such a sensor structure, in order to meet the above-described requirements, the terminal spaces of the separator are formed such that the crimp portions can be inserted from the front-end side toward the rear-end side. The terminal spaces have a reduced diameter at the rear ends thereof so as to form stop portions such that the lead wires can pass through, but the larger crimp portions come into contact with the stop portions. Therefore, during assembly of the metallic terminal members into the terminal spaces of the separator, the lead wires are inserted into the terminal spaces of the separator from the rear side thereof, and pulled out to the front side of the separator. End portions (conductors) of the pulled out lead wires are then fixed to the crimp portions of the metallic terminal members. Subsequently, the lead wires are pulled toward the rear side of the separator until the rear ends of the crimp portions contact the stop portions at the rear end of the terminal spaces, whereby rearward movement of the metallic terminal members is blocked so as to prevent the metallic terminal members from being pulled out of the separator.

Meanwhile, in the present invention, the crimp portion of the center metallic terminal member is bent in a direction opposite the bending direction of the crimp portion of the side metallic terminal members. Therefore, in the case where three electrode terminals are provided on one side surface of the element, the crimp portion of the center metallic terminal member is positioned outward in relation to the crimp portions of the side metallic terminal members which face the side surface of the sensor element. Therefore, if the terminal spaces of the spacer are formed to have identical transverse cross sections, assembly becomes very difficult. Thus, the terminal space for accommodating the center metallic terminal member must be formed such that, during assembly, the terminal space allows for passage of the crimp portion therethrough, accommodates the crimp portion, and blocks rearward movement of the crimp portion. However, since formation of such a terminal space renders the structure of the spacer complicated, formation of such a terminal space is unsuitable for the case where the spacer is made of ceramic. Further, in the case where the transverse cross section of the terminal space is increased so as to overcome the above-described problem, the thickness of the outer wall of the separator decreases. In addition, the plate spring portion of the center metallic terminal member must be increased in size as compared with the other metallic terminal members, and therefore must be prepared separately. Further, according to another possible measure, only the center metallic terminal member is assembled through an operation of inserting it into the separator from the rear-end side toward the front-end side thereof, and leaving the crimp portion at a position rearward of the rearward-facing surface of the separator. However, in this case, blocking rearward movement of the metallic terminal member cannot be secured easily, and the crimp portion is exposed at the rear end of the separator, causing a problem associated with maintaining electrical insulation.

In contrast, since the sensor according to the second aspect of the invention has the above-described structure, the sensor is not subject to problems associated with assembly of the metallic terminal members into the separator, and the size of the sensor is not increased. In addition, the separator can be easily configured. That is, in the sensor of the present invention, assembly of the metallic terminal members can be performed as follows. Here, the side metallic terminal members are assumed to have, at the front ends of the plate spring portions, engagement fingers which engage the front end of the first separator. A lead wire to be connected to the center metallic terminal member is passed through the second separator, is pulled out to the front side of the second separator, and is crimp-connected to the crimp portion of the center metallic terminal member. Subsequently, the metallic terminal member is inserted into the first separator from the rear side thereof such that the plate spring portion at the front end of the metallic terminal member is first inserted and the crimp portion is disposed in place. At that time, lead wires to be connected to the side metallic terminal members are passed through the first and second separators, are pulled out to the front side of the first separator, and are crimp-connected to the crimp portions of the corresponding metallic terminal members. Subsequently, the lead wires are pulled rearward. The front end of the second separator is brought into contact with the rear end of the first separator, whereby the assembly work is completed.

Further, in the case where the above-described engagement fingers are not provided, the assembly work may be performed as follows. Lead wires to be connected to all the metallic terminal members are passed through the second separator, are pulled out to the front side of the second separator, and are crimp-connected to the crimp portions of the corresponding metallic terminal members. Subsequently, the metallic terminal members are inserted into the first separator from the rear side thereof such that the plate spring portions at the front ends of the metallic terminal members are first inserted and that the crimp portions are disposed in place. Subsequently, the front end of the second separator is brought into contact with the rear end of the first separator. As described above, in the sensor according to the second aspect of the invention, the separator is divided into first and second separators. Therefore, even though the crimp portion of the center metallic terminal member (which faces away from the side surface of the sensor element) is positioned outward in relation to the crimp portions of the side metallic terminal members (which face the side surface of the sensor element), no problems arise in assembly thereof, and rearward movement of the crimp portions can be prevented. In addition, the structure of the terminal spaces can be simplified. That is, the terminal spaces of each separator can be straight holes extending in the front-rear direction.

Moreover, according to the above preferred embodiment, each of the metallic terminal members has a junction line portion which connects the crimp portion and the plate spring portion and which extends straight in the front-rear direction of the sensor. In this case, since the metallic terminal members can be made simple in shape, the lead wires can be smoothly passed through the center through holes and extended to the outside.

DESCRIPTION OF REFERENCE NUMERALS

Figure 1:
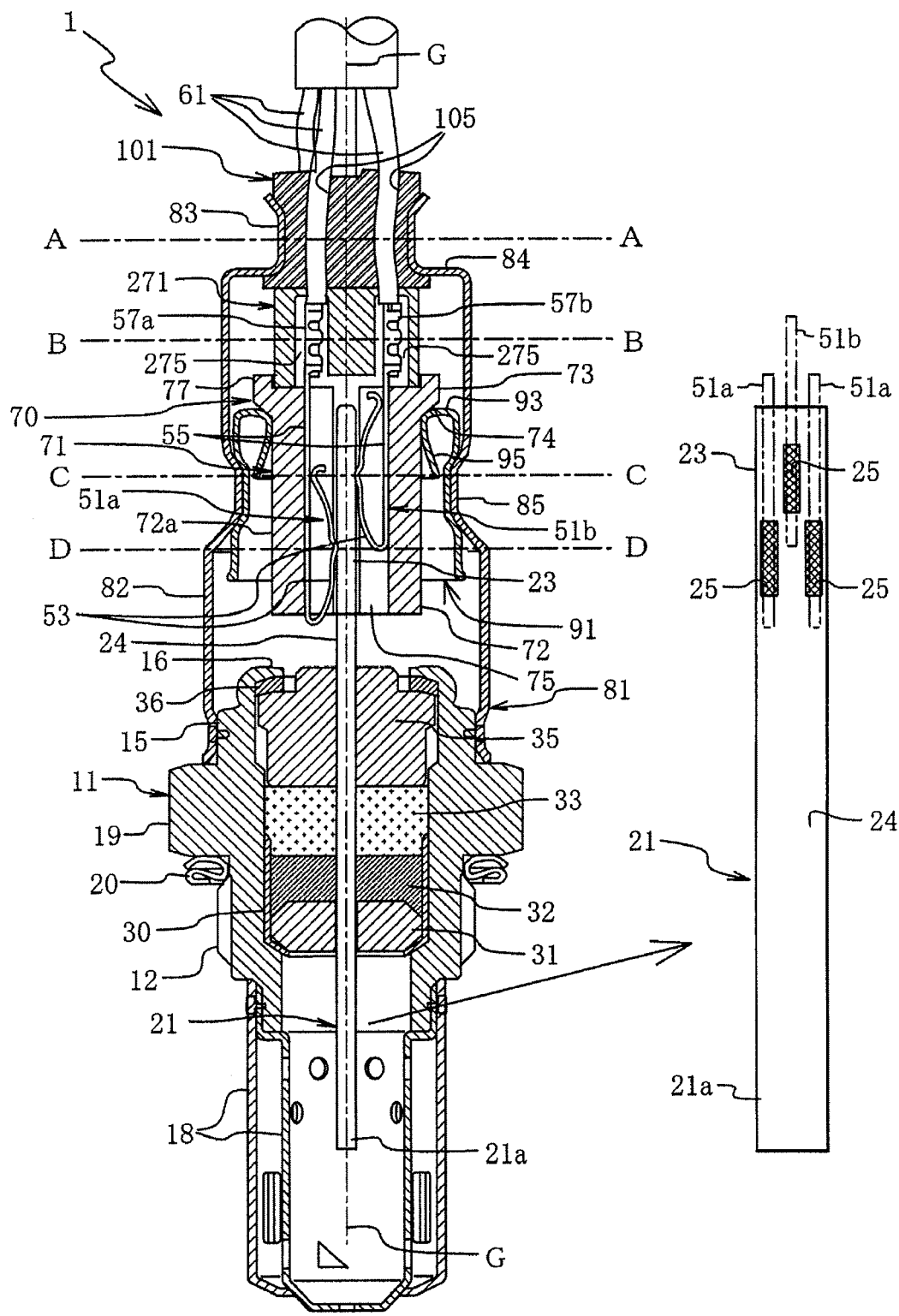
FIG. 1 is a front vertical sectional view showing an embodiment of the sensor of the present invention, and a right or left side view of the sensor element shown in the sectional view.

Reference numerals used to identify various features of the drawings include the following.
1: gas sensor
11: metallic shell body
21: sensor element
24: side surface of the sensor element
25: electrode terminal
51a, 51b: metallic terminal member
53, 53: plate spring portion
57a, 57b: crimp portion
58: crimping finger
61: lead wire
70: separator
71: first separator
271: second separator
75: terminal space
275: terminal space
101: elastic seal member
105: through hole of the elastic seal member
G: axis

DETAILED DESCRIPTION OF THE PREFERRED EMBODIMENTS

The invention will next be described in detail with reference to FIGS. 1 to 11. However, the present invention should not be construed as being limited thereto. In the present embodiment, the invention is embodied as an oxygen sensor 1 for detecting oxygen concentration in exhaust gas. Thus, the configuration of the entirety of the oxygen sensor 1 (hereinafter also simply referred to as the "sensor 1") will first be described. The oxygen sensor 1 includes a sensor element 21 which is disposed inside a tubular metallic shell body 11 (hereinafter, also simply referred to as the body 11). The sensor element 21 is formed predominantly of ceramic, has an elongated plate-like shape having a rectangular cross section, and includes a detection portion (not shown) 21a located at its front-end portion (a lower portion in the drawings). The inner circumferential surface of the metallic shell body 11 has a stepped cylindrical shape formed by concentric cylindrical surfaces such that its inside diameter increases from the front end toward the rear end. External threads 12 are formed on the outer circumferential surface of a front end portion of the metallic shell body 11, and are used to fix the metallic shell body 11 to an exhaust pipe of an engine (not shown).

Air-tightness maintaining means for maintaining air-tightness of the sensor element 21 and fixation means for fixing the sensor element 21 are disposed inside the body 11 and outside the sensor element 21. The air-tightness maintaining means and the fixation means are configured as follows: a tubular member 30 is supported by an inside step portion of the body 11; and a holder 31 and sealing materials (talc in the present embodiment) 32 and 33 are successively placed within the tubular member 30 from bottom to top. A sleeve 35 is disposed on the sealing material 33. The sleeve 35 is pressed toward the front end side via a ring washer 36 through inward bending of a crimping cylindrical portion 16 integral with a cylindrical portion 15 located at the rear end of the body 11. As a result, the sealing materials 32 and 33 and the like are compressed, whereby the sensor element 21 is airtightly fixed within the metallic shell body 11.

The thus-fixed element 21 is such that a front end portion where the detection portion 21a is located projects by a predetermined amount (length) from the front end surface of the body 11 and such that a rear end portion 23 projects by a predetermined amount (length) from the rear end of the body 11 and the rear end surface of the sleeve 35. Further, a protector 18 in which a plurality holes are formed and which has a dual structure is provided on the front end side of the sensor element 21 in such a manner as to surround a front end portion of the sensor element 21. This protector 18 is fitted onto and fixed to the front end of the body 11. Notably, a large-diameter portion 19 projecting radially outward, which is formed on the body 11 at an intermediate portion with respect to the direction of the axis G, is a polygonal portion used for attaching the body 11 to an exhaust pipe (not shown). A sealing gasket 20 is attached to the lower surface of the polygonal portion.

Figure 11:
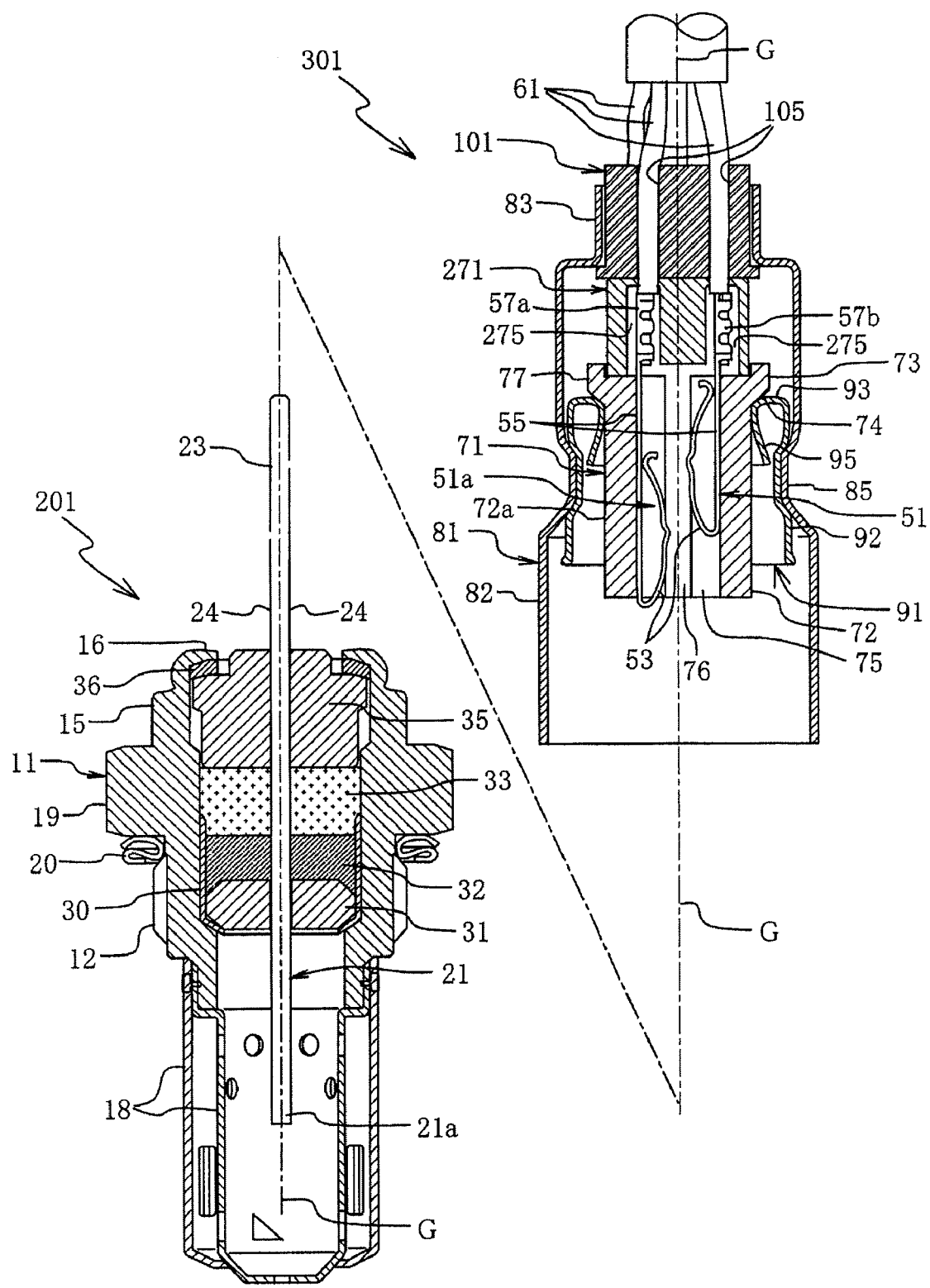
FIG. 11 is a view which illustrates a step of assembling the sensor of FIG. 1.
Figure 12:
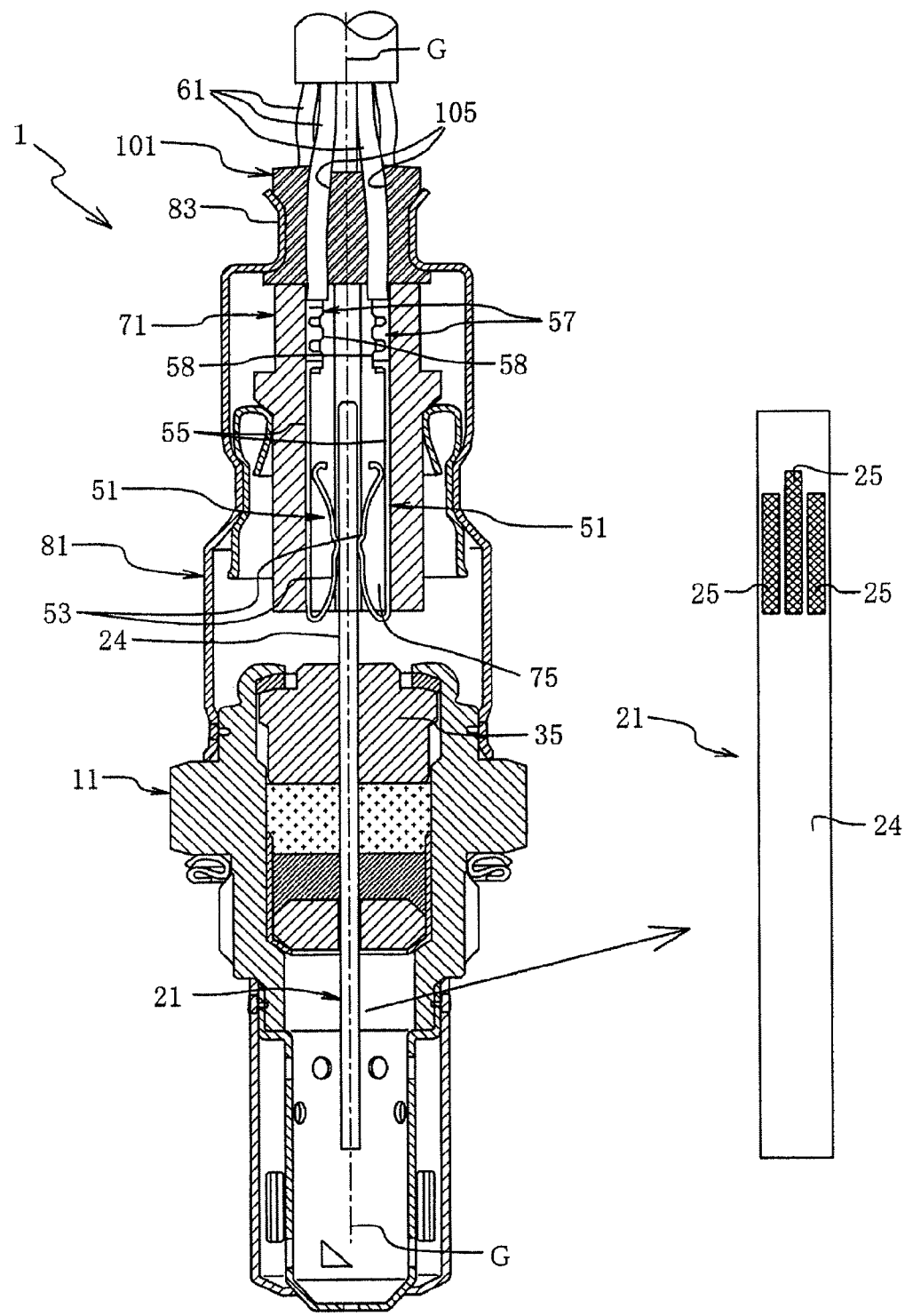
FIG. 12 is a front vertical sectional view showing a conventional sensor and a right side view of the sensor element shown in the sectional view.
Figure 13:
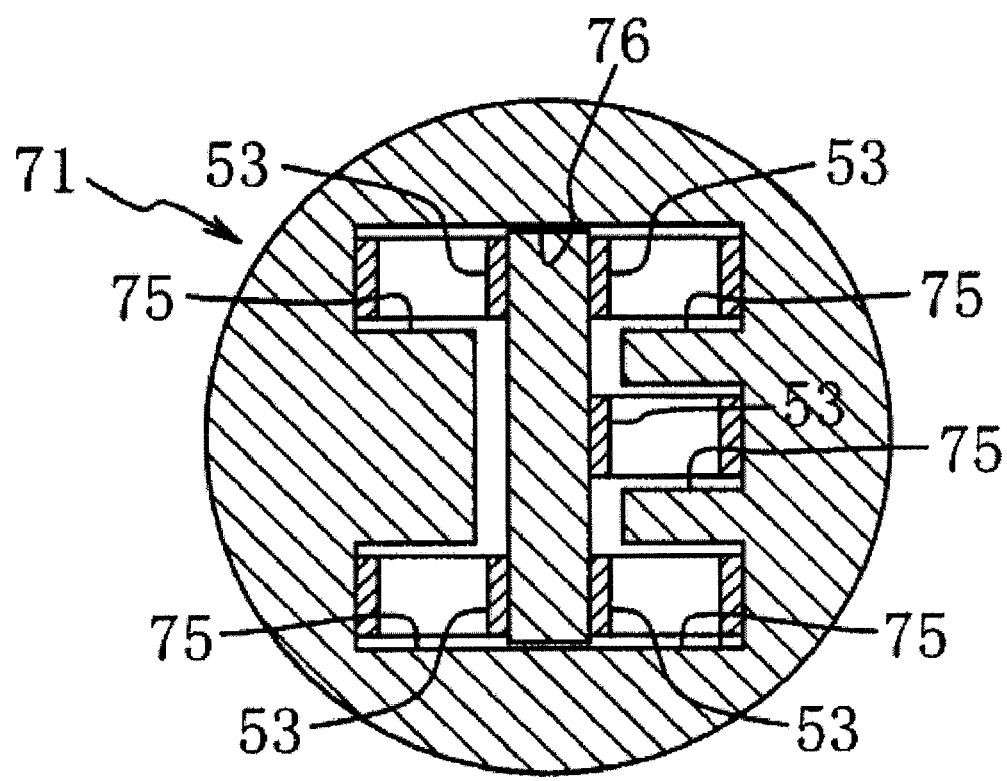
FIG. 13 is a traverse cross sectional view of the separator of FIG. 12.
Figure 14:
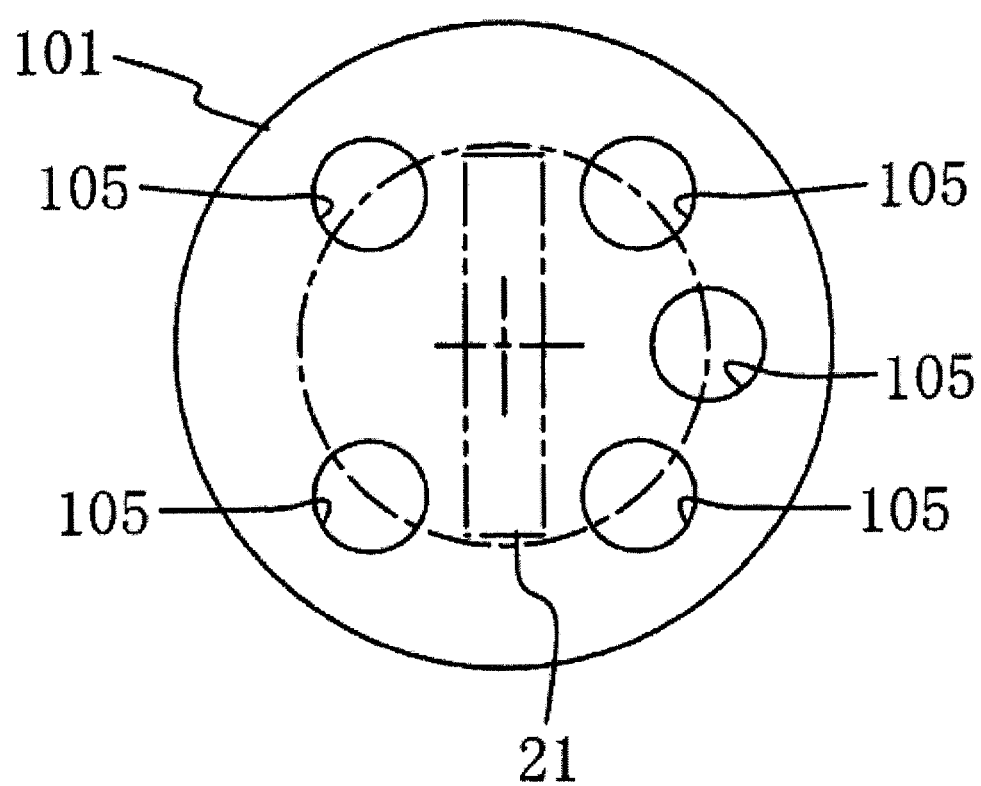
FIG. 14 is an explanatory view of the elastic seal member of the sensor of FIG. 12, as viewed from the rear side.

As in the case of the sensor element 21 shown in FIG. 12, a plurality of (e.g., three) electrode elements 25 are formed on opposite side surfaces 24 of the rear end portion 23 of the element 21 fixedly disposed inside the body 11, the rear end portion 23 projecting from the rear end of the sleeve 35. As shown on the right-hand side in FIG. 1, the electrode elements 25 are arranged laterally. In the present embodiment, in relation to the two electrode terminals 25 located on opposite lateral ends, the electrode terminal 25 located (at an intermediate position) between the two electrode terminals 25 is located rearward, so that the center electrode terminal 25 does not overlap the remaining electrode terminals 25 with respect to the front-rear direction (the vertical direction in FIG. 1). These electrode terminals 25 include those for outputting a detection output from the detection section 21a, and those for applying a voltage to an unillustrated heater formed in the element 21. The above-described components of the sensor 1 of the present embodiment correspond to an element-side half assembly 201, in which the sensor element 21 is fixedly disposed within the body 11, and which is shown in the lower left drawing of FIG. 11 described below.

Meanwhile, on the rear-end side of the metallic shell body 11, a cylindrical, tubular separator 70 formed of an insulating material (ceramic) is disposed coaxially with the metallic shell body 11. The rear end portion 23 of the sensor element 21 is inserted into a central portion of the separator 70. The separator 70 is composed of a first separator 71 located on the front-end side and a second separator 271 located on the rear-end side. Both the first and second separators 71 and 271 have a cylindrical outer circumferential surface. The second separator 271 is disposed coaxially with the first separator 71 such that the front end of the second separator 271 is in contact with the rear end of the first separator 71.

The first separator 71 has a cylindrical tubular portion 72 and a flange 73 provided at the rear end of the cylindrical tubular portion 72 and projecting outward from an outer circumferential surface 72a thereof. An annular portion 77 is provided at the rear end of the flange 73 coaxially with the axis G The annular portion 77 projects in the form of an annular ring. The first separator 71 has a central hole portion 76 (see FIG. 7) and terminal spaces 75, which extend through the first separator 71 in the front-rear direction, in order to accommodate the element 21 at the center and to accommodate plate spring portions 53 of metallic terminal members 51a and 51b in a state where the plate spring portions 53 are pressed against the electrode terminals 25 on the side surfaces 24 of the element 21. The first separator 71 has walls 78 (see FIG. 5) which extend in the front-rear direction and provide insulation between adjacent metallic terminal members.

Figure 4:
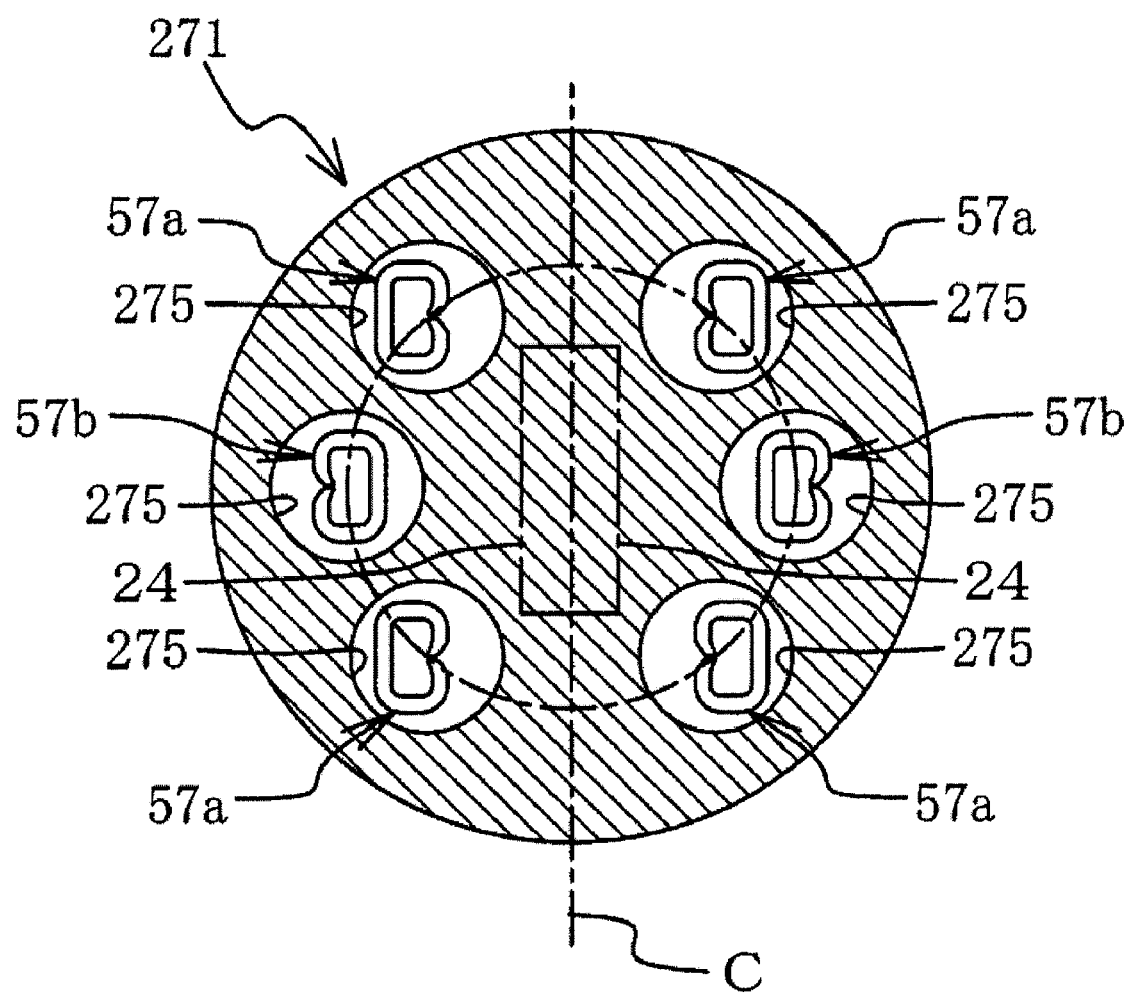
FIG. 4 is an enlarged cross sectional view of the second separator taken along line B-B of FIGS. 1 and 2.

Meanwhile, the second separator 271 assumes a cylindrical columnar shape, and is disposed such that its front end comes into contact with the rear end of the first separator 71 and fits into the space surrounded by the annular portion 77. The second separator 271 has terminal spaces 275 for accommodating crimp portions 57a and 57b of the metallic terminal members. The terminal spaces 275 are provided such that they extend through the second separator 271 in the front-rear direction at positions corresponding to those of the terminal spaces 75 of the first separator 71. The terminal spaces 275 have a circular transverse cross section, and are provided along a circle as viewed in the direction of the axis G. That is, the terminal space 275 which accommodates the crimp portion 57b of the center metallic terminal member 51b of the three metallic terminal members to be connected to the electrode terminals 25 on one side surface 24 of the element 21 is separated outward from a center line C between the two side surfaces 24 of the element 21 by a greater distance, as compared with the terminal spaces 275 located at opposite lateral ends, as shown in FIG. 4. Notably, the inner diameters of the terminal spaces 275 of the second separator 271 are reduced at the end portions thereof so as to permit passage of the lead wires 61 therethrough but prohibit passage of the crimp portions therethrough, to thereby prevent rearward movement of the crimp portions.

Next, the metallic terminal members 51a and 51b will be described. Each of the metallic terminal members 51a and 51b is formed from a metallic plate having resiliency, and includes a plate spring portion 53 provided at the front end and bent into a folded-back shape; and a crimp portion 57a or 57b provided at the end (rear end) opposite to the spring plate portion 53 such that the crimp portion connects to the spring plate portion 53 via a junction line portion 55. The plate spring portion 53 is resiliently pressed against the corresponding electrode terminal 25, whereby each metallic terminal member is electrically connected to a corresponding electrode terminal 25.

Figure 2:
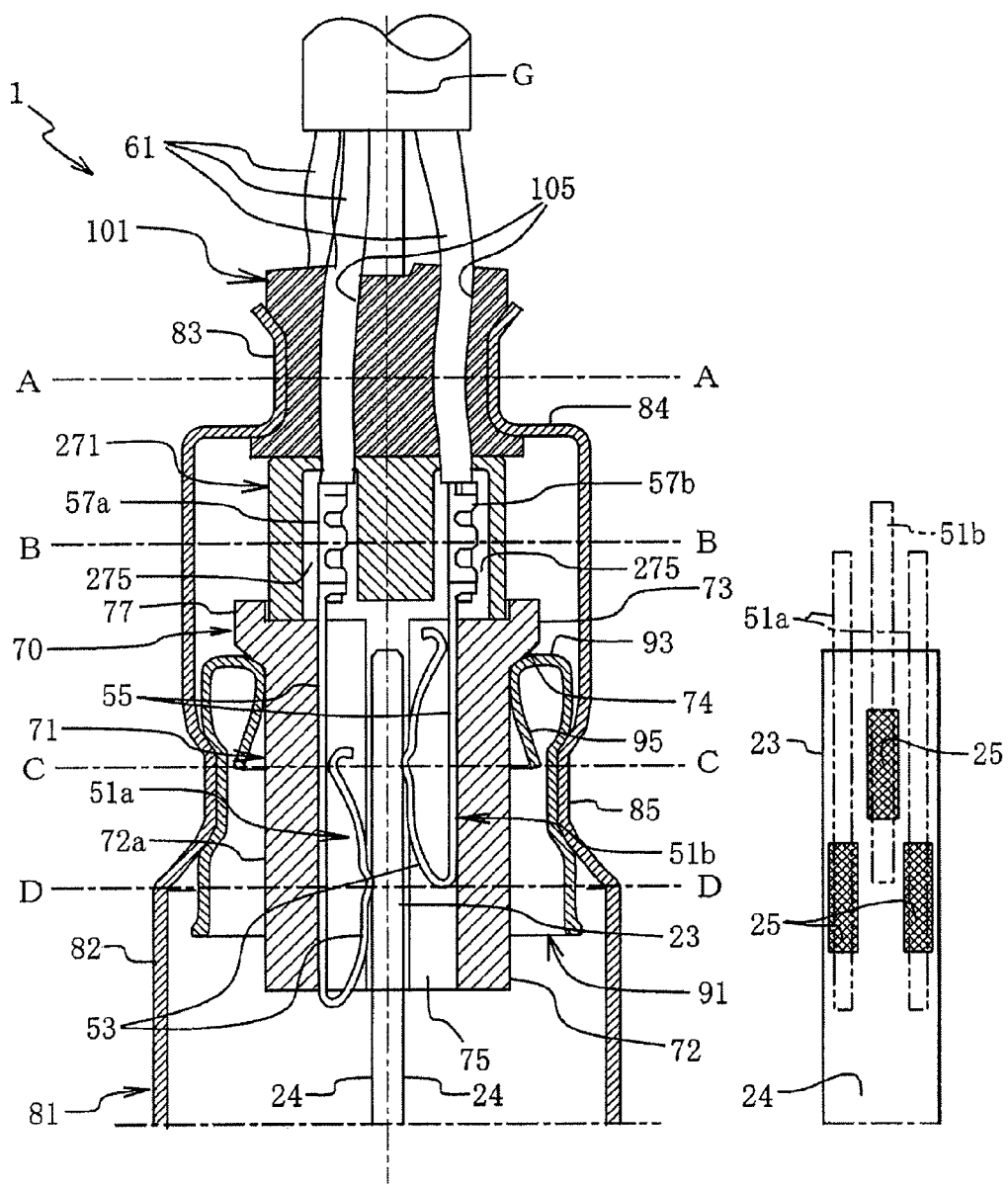
FIG. 2 is an enlarged view of a main portion of FIG. 1.
Figure 3:
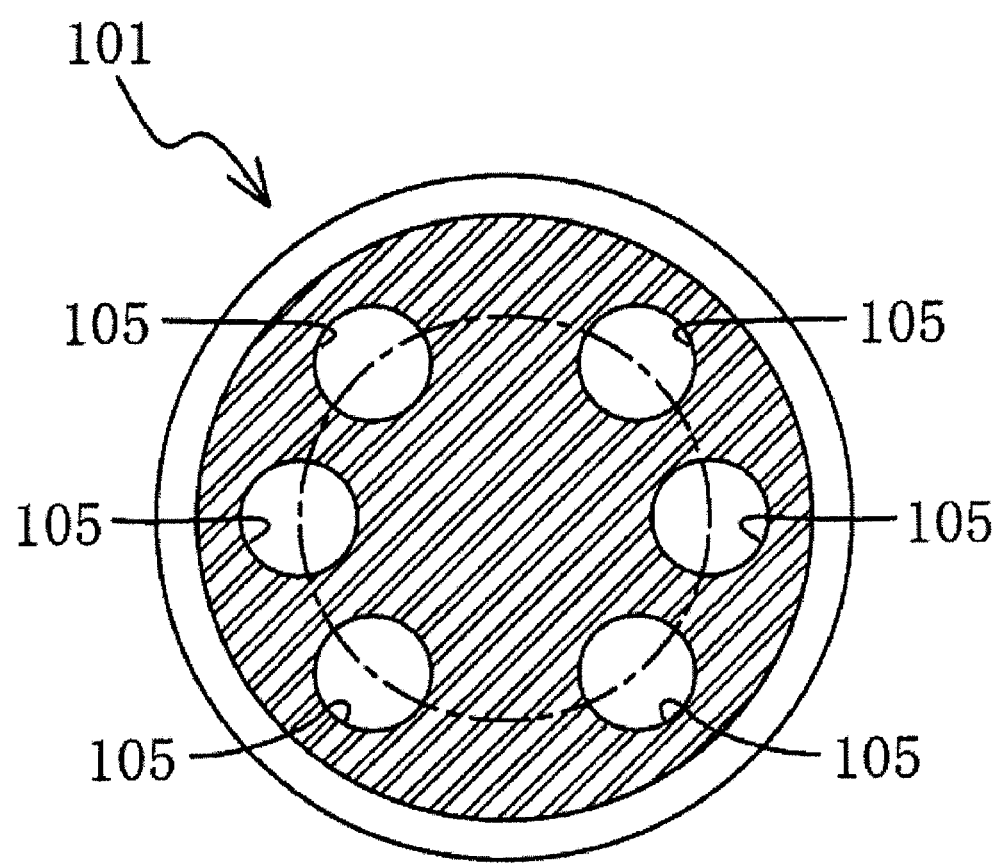
FIG. 3 is an enlarged cross sectional view of the elastic seal member taken along line A-A of FIGS. 1 and 2, with the lead wires omitted.
Figure 5:
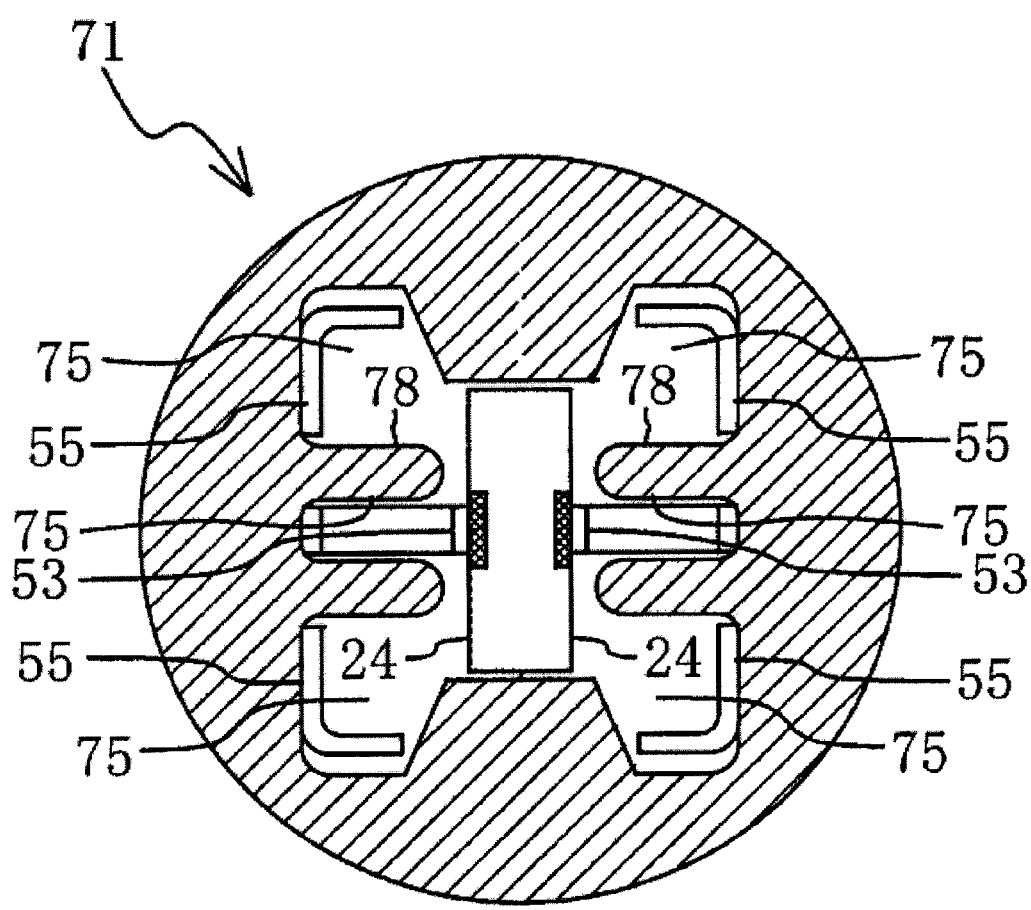
FIG. 5 is an enlarged cross sectional view of the first separator taken along line C-C of FIGS. 1 and 2.
Figure 6:
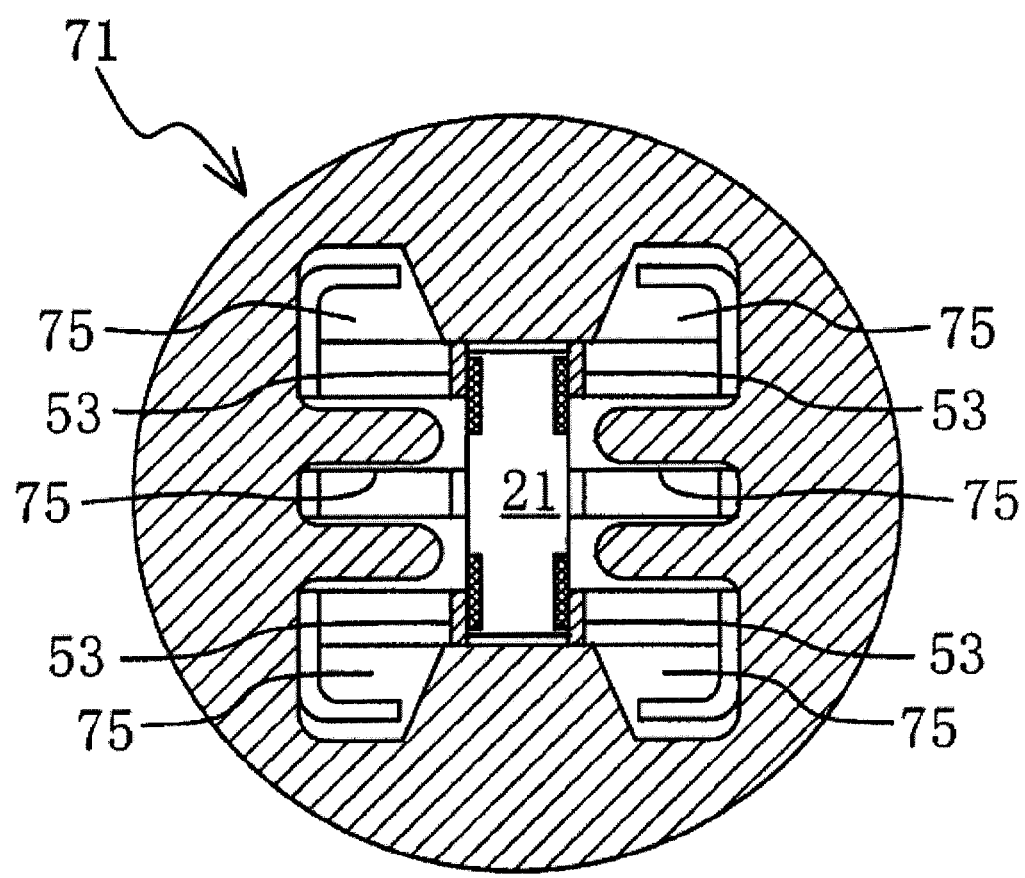
FIG. 6 is an enlarged cross sectional view of the first separator taken along line D-D of FIGS. 1 and 2.
Figure 7:
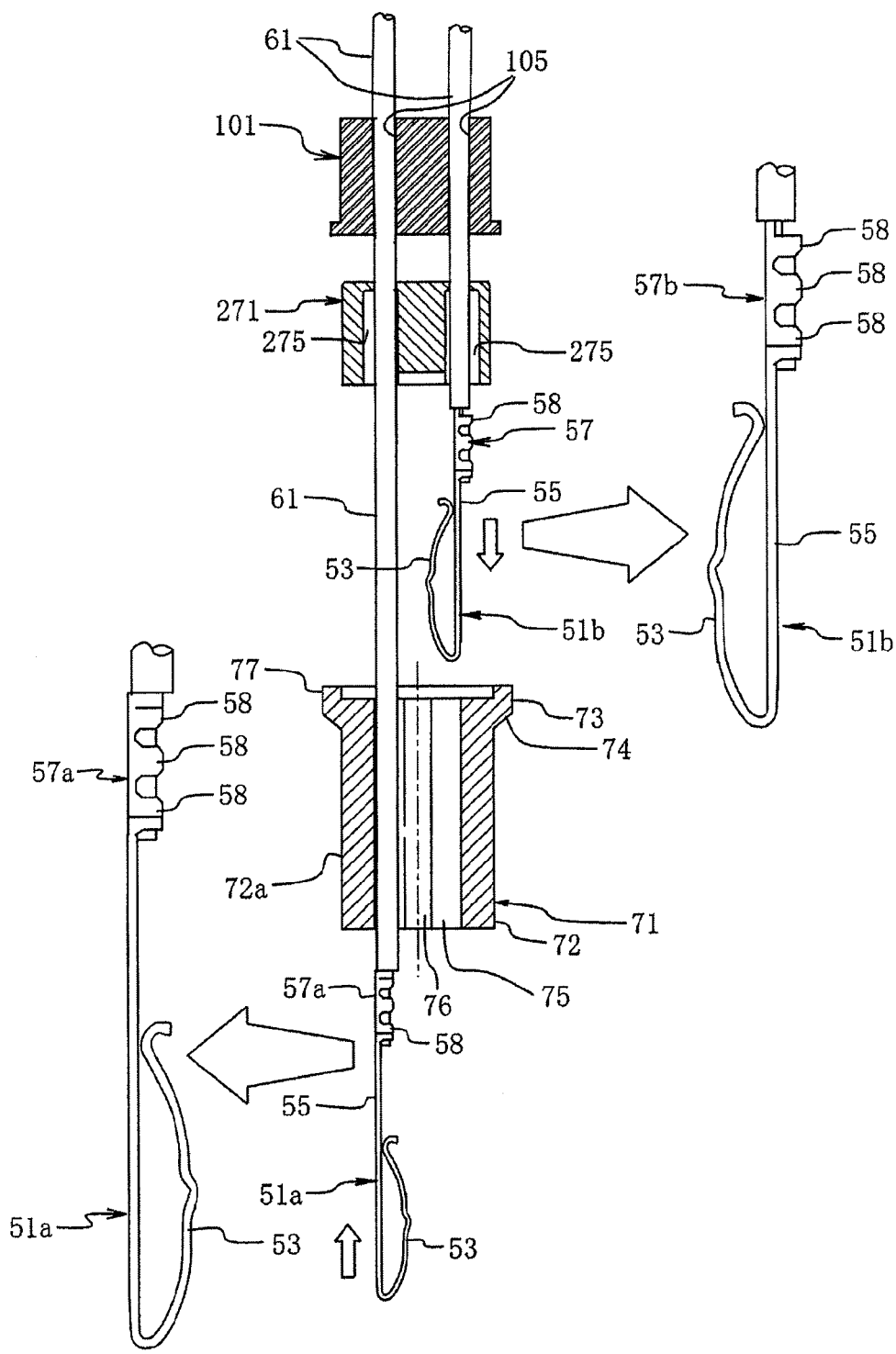
FIG. 7 is an exploded vertical sectional view which illustrates a step of assembling the metallic terminal members into the first and second separators, and includes enlarged views of the metallic terminal members.
Figure 8:
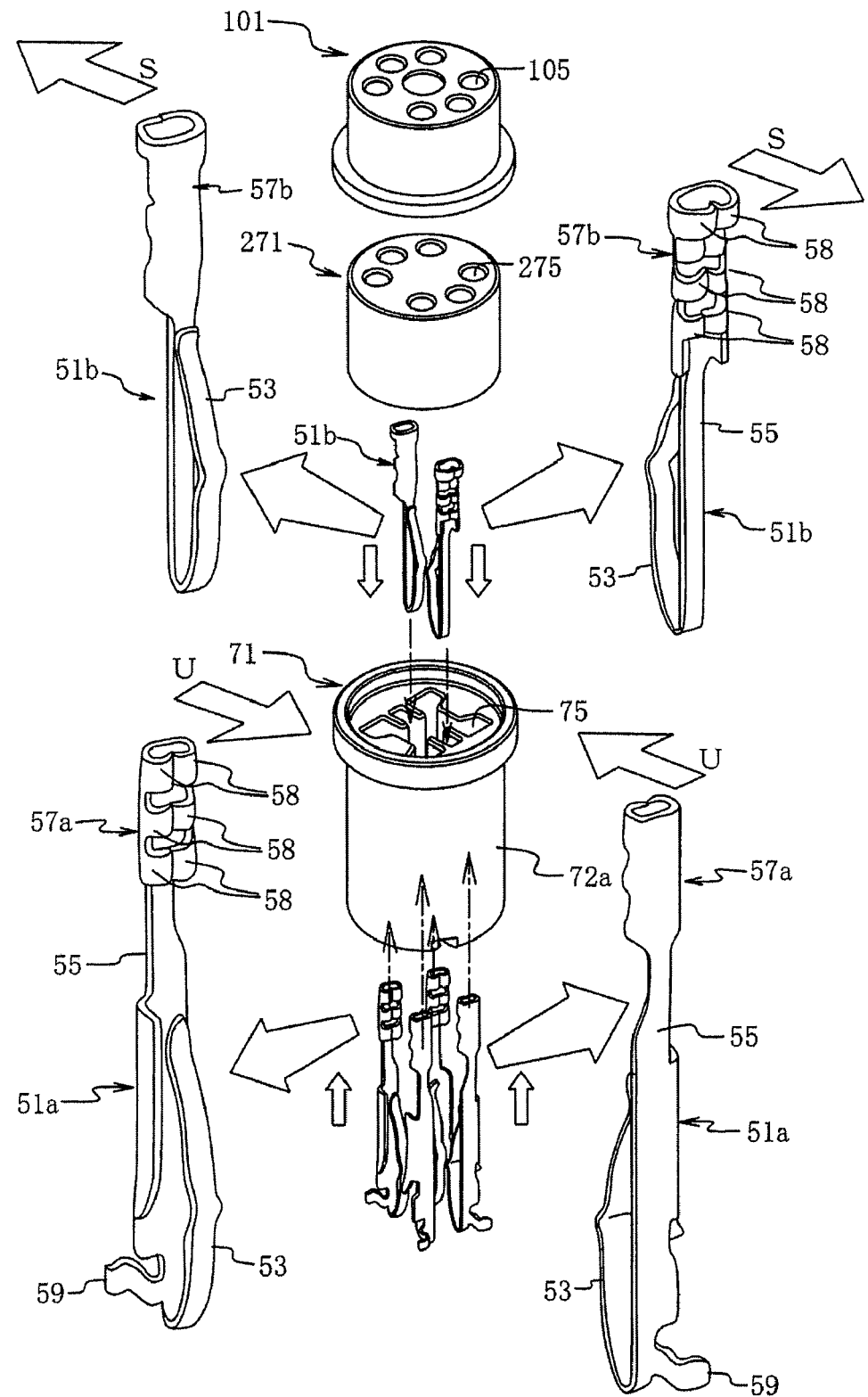
FIG. 8 is an exploded perspective view which illustrates the step of assembling the metallic terminal members into the first and second separators, and includes enlarged views of the metallic terminal members.
Figure 9:
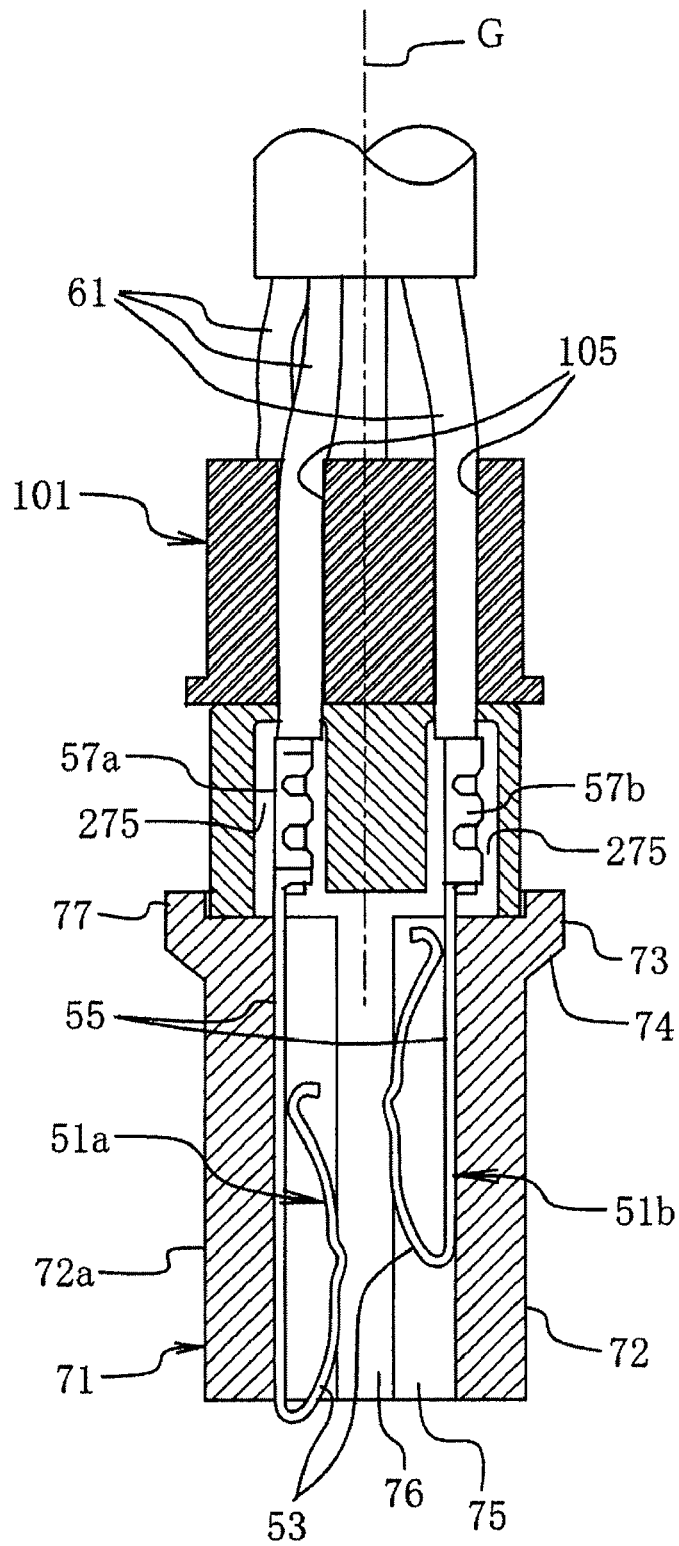
FIG. 9 is an enlarged vertical cross sectional view showing a state in which the metallic terminal members and associated lead wires are assembled to the first and second separators.
Figure 10:
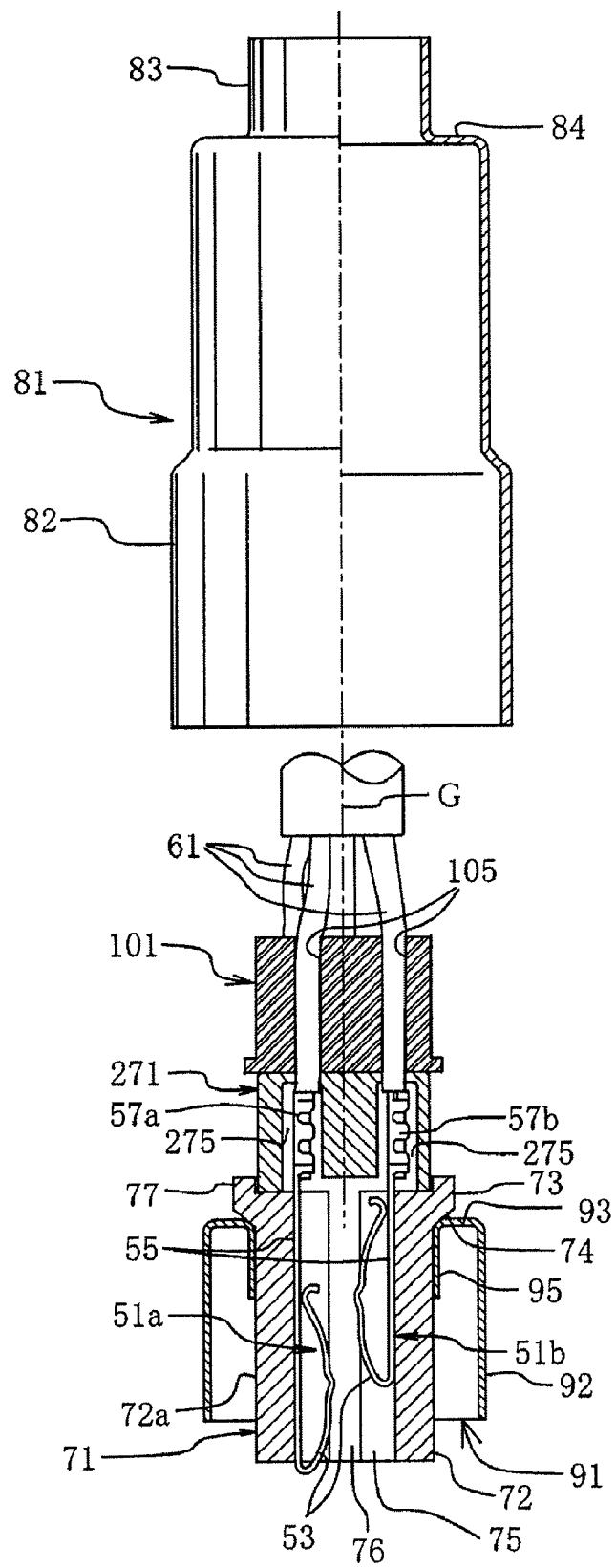
FIG. 10 is a vertical cross sectional view which illustrates a step of assembling the protection sleeve after the assembly step of FIG. 9.

Each of the crimp portions 57a and 57b provided at the rear ends of the metallic terminal members 51a and 51b has crimping fingers 58 along opposite sides. The crimping fingers 58 of the crimp portions 57a of the metallic terminal members 51a located at the opposite lateral ends (hereinafter also referred to as the "side metallic terminal members 51a") are bent toward the side where the electrode terminals 25 are present, whereby the corresponding leads wires 61 are fixed to the crimp portions 57a. Notably, in FIGS. 1 and 2, one of the side metallic terminal members 51a is shown on the left side of the axis G, and its crimping fingers 58 face toward the sensor element 21 (the right side in FIGS. 1 and 2). Meanwhile, the crimping fingers 58 of the crimp portion 57b of the center metallic terminal member 51b are bent toward a direction opposite the electrode terminals 25, whereby the corresponding leads wire 61 is fixed to the center crimp portions 57b. Notably, in FIGS. 1 and 2, the center metallic terminal member 51b is shown on the right side of the axis G, and its crimping fingers 58 face toward a direction opposite the sensor element 21 (the right side in FIGS. 1 and 2). Therefore, the terminal space 275 for accommodating the crimp portion 57b of the center metallic terminal member 51b is provided at an outward shifted position (see FIG. 4). Further, as shown in FIGS. 5, 6 and 8, the side metallic terminal members 51a are each formed such that the junction line portion 55 is bent outward, and an engagement finger 59 engaging the front end of the first separator 71 projects outward from the front end of the metallic terminal member (see FIG. 8). Notably, as shown in FIGS. 1 and 2, the distance between the crimp portion 57*b* and the plate spring portion 53 of each metallic terminal member 51*b* is made shorter than that between the crimp portion 57*a* and the plate spring portion 53 of each metallic terminal member 51*a*, to thereby improve the reliability of electrical connection with the electrode terminals 25.

The lead wires 61 are passed through through holes 105 of an elastic seal member 101 and extended to the outside from the rear end of a protection sleeve 81 formed of a metal. Notably, the front end of the elastic seal member 101 is configured so as to press the rear end of the second separator 271 toward the front-end side when compressed.

The protection sleeve 81 is disposed on the radially outer side of the first separator 71 and the second separator 271 so as to surround them. The protection sleeve 81 includes a smaller-diameter portion 83 formed at the rear end via an annular shoulder portion 84. The smaller-diameter portion 83 is formed such that it has a relatively small diameter and assumes a cylindrical tubular shape. The protection sleeve 81 also includes a larger-diameter portion 82 formed on the front-end side in relation to the annular shoulder portion 84 and having a diameter greater than that of the smaller-diameter portion 83. The front end of the protection sleeve 81 is fitted onto a rear-end-side cylindrical portion 15 of the metallic shell body 11, and welded thereto after being crimped, whereby the protection sleeve 81 is fixed to the body 11.

Notably, in the present embodiment, a cylindrical, tubular support member 91 for supporting the separator 70 is coaxially disposed in an annular space between the inner circumferential surface of the larger-diameter portion 82 of the protection sleeve 81 and the first separator 71, and fixed to the inner surface of the protection sleeve 81. This support member 91 is formed of a metal plate (thin plate), and includes a tubular plate wall portion 92 (see FIG. 11) formed into a generally tubular cylindrical shape. The support member 91 also includes a spring portion 95, which is formed by bending, into a folded-back shape, an inside portion of an inward-extending flange, which is formed by inwardly bending a rear end portion 93 of the tubular plate wall portion 92. As a result of an intermediate portion of the larger-diameter portion 82 of the protection sleeve 81 being crimped so as to reduce the diameter of the larger-diameter portion 82, the support member 91 is deformed toward the axis G. As a result of this deformation, the spring portion 95 is pressed against the outer circumferential surface 72*a* of the first separator 71, and the support member 91 is fixedly disposed within the protection sleeve 81. In the present embodiment, the folded-back portion (the rear end portion 93) of the support member 91 is disposed such that the folded-back portion engages a frontward-facing surface 74 of the flange 73 of the first separator 71, whereby movement of the first separator 71 toward the front-end side is restricted.

Next, the elastic seal member 101 will be described. This elastic seal member 101 assumes a generally cylindrical columnar shape, and includes through holes 105, which have a circular transverse cross section and through which the lead wires 61 are passed. The through holes 105 are provided in the same layout as the terminal spaces 275 of the second separator 271. Therefore, like the layout of the terminal spaces 275, as viewed from the rear side, the through holes 105 are provided along a circle in such a manner that the center through hole (which receives the lead wire 61 to be connected to the center metallic terminal member 51*b* of the three metallic terminal members to be connected to the electrode terminals 25 on one side surface 24 of the element 21) is located outward in relation to the through holes located at opposite sides of the center through hole. Notably, the through hole 105 has such a diameter that, when the elastic seal member 101 is in a free state, substantially no clearance is formed between the wall surfaces of the through hole 105 and the lead wires 61 passed therethrough.

In the present embodiment, the elastic seal member 101, through which the lead wires 61 are passed in the front-rear direction, is placed inside the smaller-diameter portion 83 of the protection sleeve 81 in a state in which the front end of the elastic seal member 101 is in contact with the rear end (the upper end in the drawings) of the second separator 271. In this state, the smaller-diameter portion 83 is crimped to reduce its diameter, to thereby compress the elastic seal member 101 in the radial direction, whereby sealing is provided between the inner circumferential surface of the smaller-diameter portion 83 and the outer circumferential surface of the elastic seal member 101 and between the wall surfaces of the through holes 105 and the outer circumferential surfaces of the lead wires 61. Notably, the elastic seal member 101 is formed of, for example, fluoro rubber.

Assembly of a metallic-terminal-member-side half assembly 301 shown in the upper right drawing of FIG. 11 will be described in detail (see FIGS. 7 to 11). That is, the leading ends of the lead wires 61 are passed through the through holes (for insertion of the lead wires) 105 of the elastic seal member 101, and are passed through the terminal spaces 275 provided within the second separator 271. Moreover, the lead wires 61, excluding the lead wires to be connected to the center metallic terminal members 51*b*, are passed through the corresponding terminal spaces 75 provided within the first separator 71. Then, the crimp portions 57*a* and 57*b* of the metallic terminal members 51*a* and 51*b* are crimp-connected to the conductors of the corresponding lead wires 61, by bending the crimping fingers 58 as described above. As shown in the lower side of FIG. 8, the crimp portions 57*a* of the side metallic terminal members 51*a* are crimped in such a manner that the bent crimping fingers 58 thereof face inward (indicated by arrow U), and the crimp portions 57*b* of the center metallic terminal members 51*b* are crimped in such a manner that the bent crimping fingers 58 thereof face outward (indicated by arrow S). The lead wires 61 are pulled from the rear side of the second separator 271, while the orientations of the crimp portions 57*a* and 57*b* are maintained. Also, the plate spring portions 53 of the metallic terminal members are inserted into the terminal spaces 75 of the first separator 71 such that the plate spring portions 53 are arranged as described manner. The crimp portions projecting rearward from the first separator 71 are inserted into the terminal spaces 275 of the second separator 271. Next, the front end of the elastic seal member 101 is brought into contact with the rear end of the second separator 271 (see FIG. 9).

Subsequently, the support member 91 is fitted onto the outer circumferential surface 72*a* of the first separator 71 from the front end side thereof in such a manner that the rear end 93 of the support member 91 comes into contact with the frontward-facing surface 74 of the flange 73. Next, the protection sleeve 81 is placed to cover the elastic seal member 101 and the first and second separators from the rear side in such a manner as to surround the elastic seal member 101 and the first and second separators (see FIG. 10). Next, in this state, a portion 85 of the larger-diameter portion 82 of the protection sleeve 81, the portion corresponding to an intermediate portion of the support member 91 with respect to the front-rear direction, is crimped such that the diameter of the portion 85 is reduced (the portion 85 is constricted) (see the upper right drawing of FIG. 11).

The metallic-terminal-member-side half assembly 301 assembled as described above is positioned in such a manner that its axis G coincides with that of the element-side half assembly 201 and that the rear end portion 23 of the sensor element 21 of the element-side half assembly 201 is located between the opposed metallic terminal members 51a and 51b within the first and second separator 71 and 271 of the metallic-terminal-member-side half assembly 301, as shown in FIG. 11. Subsequently, the half assemblies are caused to approach each other, whereby the rear end portion 23 of the element 21 is inserted between the opposed metallic terminal members 51a and 51b, and the plate spring portions 53 of these metallic terminal members are pressed against the electrode terminals 25 of the sensor element 21. The front end portion of the larger-diameter portion 82 of the protection sleeve 81 is then fitted onto the rear-end-side cylindrical portion 15 of the metallic shell body 11, and the fitted portion is crimped from the outer circumferential side, followed by welding for fixing. Subsequently, the smaller-diameter portion 83 provided at the rear end (the upper end in the drawing) of the protection sleeve 81 is crimped in such a manner as to reduce its diameter, to thereby compress and fix the elastic seal member 101 in the radial direction. By virtue of such a procedure, as described above, sealing is provided between the inner circumferential surface of the rear end portion of the protection sleeve 81 and the outer circumferential surface of the elastic seal member 101 and at the outer circumferential surfaces of the lead wires 61 extending through the through holes 105.

The sensor 1 of the present embodiment is assembled as described above. In its structure, as described above, the crimping fingers 58 of the crimp portions 57b of the center metallic terminal members 51b connected to the center electrode terminals 25 are bent outward (rightward in FIGS. 1 and 2), as shown on the right side of the axis G in FIGS. 1 and 2 (see FIG. 4). This bending direction is opposite that of the crimping fingers 58 of the crimp portions 57a of the side metallic terminal members 51a shown on the left side of the axis G in FIGS. 1 and 2. Therefore, as viewed in the axial direction, the crimp portions 57b of the center metallic terminal members 51b are separated outward from the element 21 by a larger amount, as compared with the crimp portions 57a of the side metallic terminal members 51a. Accordingly, even in the case where the center through holes 105 of the elastic seal member 101 are located outward in relation to the side through holes 105 as in the present embodiment, the lead wires 61 connected to the center metallic terminal members 51b can be passed through the corresponding through holes more easily, as compared with the case where the crimp portions of all the metallic terminal members face the electrode terminals on the side surfaces of the element as in conventional sensors.

In addition, in the present embodiment, the separator is composed of two members; i.e., the first and second separators 71 and 271. Therefore, despite the crimp portions 57b of the center metallic terminal members 51b facing outward, assembly work can be smoothly performed without causing any problem. Further, in the present embodiment, rearward movement of the crimp portions 57a and 57b can be prevented by means of the second separator 271 as well. Moreover, since the separator is composed of two members; i.e., the first and second separators 71 and 271, the structure of the terminal spaces of the separators can be kept simple. That is, since the terminal spaces of the first and second separators 71 and 271 can be straight holes extending in the front-rear direction, fabricating the separator from ceramic can be facilitated.

The sensor of the present invention is not limited to that described above, and may be properly modified without departing from the gist of the present invention. For example, in the above-described embodiment, three electrode terminals 25 are provided on each of the two side surfaces 24 of the sensor element 21. However, the number of electrode terminals 25 is not limited thereto. Further, in the above-described embodiment, the separator is composed of two parts. However, needless to say, a single-body separator may be used so long as the terminal spaces are formed such that the metallic terminal members can be assembled to the spacer. Further, in the above-described embodiment, the sensor of the present invention is embodied as a gas sensor. However, the sensor of the present invention may be embodied as another type of sensor, such as a temperature sensor.

It should further be apparent to those skilled in the art that various changes in form and detail of the invention as shown and described above may be made. It is intended that such changes be included within the spirit and scope of the claims appended hereto.

This application is based on Japanese Patent Application No. JP filed Mar. 6, 2009, incorporated herein by reference in its entirety.

What is claimed is:

1. A sensor comprising a plate-shaped sensor element extending in a front-rear direction and having a plurality of electrode terminals; a plurality of metallic terminal members connected to the electrode terminals of the sensor element; and a separator surrounding and insulating the plurality of metallic terminal members, wherein at least three electrode terminals are provided on each of opposing side surfaces of the sensor element at intervals in a lateral direction normal to the front-rear direction;

individual ones of the plurality of metallic terminal members each has a plate spring portion formed at a front end thereof, and a crimp portion formed at a rear end thereof and connecting to the plate spring portion;

the plate spring portion is pressed against the corresponding electrode terminal to thereby electrically connect the plate spring portion to the electrode terminal;

a lead wire is crimp-connected to the crimp portion to thereby electrically connect the lead wire to the crimp portion; and the lead wire is passed through one of a plurality of through holes of an elastic seal member disposed on the rear-end side of the separator, and is extended to the outside, the through holes being formed in the elastic seal member generally along a circle, wherein:

of the metallic terminal members connected to the at least three electrode terminals on each of opposing side surfaces of the sensor element, pairs of side metallic terminal members located at opposite ends with respect to the lateral direction are crimp-connected to lead wires by means of crimping fingers of the crimp portions of the side metallic terminal members that are each bent toward the side where the electrode terminals are present; and a remaining metallic terminal member connected to one of the at least three electrode terminals on each of opposing side surfaces of the sensor element and located between the side metallic terminals along the lateral direction is crimp-connected to a lead wire by means of crimping fingers of the crimp portion of the remaining metallic terminal member that are bent toward the side opposite the side where the electrode terminals are present.

2. A sensor comprising a plate-shaped sensor element extending in a front-rear direction and having a plurality of electrode terminals; a plurality of metallic terminal members connected to the electrode terminals of the sensor element; and a separator surrounding and insulating the plurality of metallic terminal members, wherein at least three electrode terminals are provided on each of opposing side surfaces of the sensor element at intervals in a lateral direction normal to the front-rear direction;

individual ones of the plurality of metallic terminal members each has a plate spring portion formed at a front end thereof, and a crimp portion formed at a rear end thereof and connecting to the plate spring portion;

the plate spring portion is pressed against the corresponding electrode terminal to thereby electrically connect the plate spring portion to the electrode terminal;

a lead wire is crimp-connected to the crimp portion to thereby electrically connect the lead wire to the crimp portion; and the lead wire is passed through one of a plurality of through holes of an elastic seal member disposed on the rear-end side of the separator, and is extended to the outside, the through holes being formed in the elastic seal member generally along a circle, wherein the separator comprises a first separator located on the front end side and a second separator located on the rear end side;

of the metallic terminal members connected to the at least three electrode terminals on each of opposing side surfaces of the sensor element, side metallic terminal members located at opposite ends with respect to the lateral direction are crimp-connected to lead wires by means of crimping fingers of the crimp portions of the side metallic terminal members that are bent toward the side where the electrode terminals are present;

a remaining metallic terminal member connected to one of the at least three electrode terminals on each of opposing side surfaces of the sensor element and located between the side metallic terminals along the lateral direction is crimp-connected to a lead wire by means of crimping fingers of the crimp portion of the remaining metallic terminal members that are bent toward the side opposite the side where the electrode terminals are present;

the plate spring portions of the metallic terminal members are accommodated in terminal spaces formed in the first separator; and the crimp portions of the metallic terminal members are accommodated in terminal spaces formed in the second separator, wherein rearward movement of the crimp portions of the metallic terminal members is blocked at rear ends of the terminal spaces of the second separator.

3. The sensor according to claim 1, wherein individual ones of the plurality of metallic terminal members each has a junction line portion which connects the crimp portion and the plate spring portion and which extends straight in the front-rear direction of the sensor element.

4. The sensor according to claim 2, wherein individual ones of the plurality of metallic terminal members each has a junction line portion which connects the crimp portion and the plate spring portion and which extends straight in the front-rear direction of the sensor element.

5. The sensor according to claim 1, wherein on each of opposing side surfaces of the sensor element, the crimping fingers extend from a flat portion of each of the crimp portions of the respective metallic terminals, and wherein the flat portions of the side metallic terminal members and the flat portion of the remaining metallic terminal between the side metallic terminal members are substantially aligned with one another in the lateral direction.

\* \* \* \* \*